US00PP35389P2

(12) United States Plant Patent
Moon

(10) Patent No.: US PP35,389 P2
(45) Date of Patent: Sep. 19, 2023

(54) ***QUERCUS ALBA* TREE NAMED 'QAMTF'**

(50) Latin Name: *Quercus alba*
Varietal Denomination: QAMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/903,679

(22) Filed: Sep. 6, 2022

(51) Int. Cl.
*A01H 5/00* (2018.01)
*A01H 6/00* (2018.01)

(52) U.S. Cl.
USPC ..... Plt./225

(58) Field of Classification Search
USPC ..... Plt./216, 225
See application file for complete search history.

*Primary Examiner* — Susan McCormick Ewoldt
(74) *Attorney, Agent, or Firm* — Cassandra Bright

(57) ABSTRACT

A new and distinct *Quercus alba* tree named 'QAMTF' is disclosed, characterized by a unique, upright, fastigiate structure with a central leader. Foliage is deeply lobed and colored deep green a somewhat blue hue. Trees have shown suitability for commercial digging and transplanting. The new variety is a *Quercus* tree, typically used for landscapes and gardens.

4 Drawing Sheets

Latin name of the genus and species: *Quercus alba.*
Variety denomination: 'QAMTF'.

BACKGROUND OF THE INVENTION

The new cultivar is a product of a planned breeding program. The new variety was discovered growing as a seedling among a group of open-pollinated *Quercus alba* trees at a tree farm in Washington, Ga. A single seedling tree was observed which had a more upright and fastigiate habit than the other seedlings among this group. The inventor made this discovery during 2012. The exact seed and pollen parents cannot be identified.

Asexual reproduction by grafting of the new cultivar 'QAMTF' was first performed during Winter of 2014 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Quercus alba* tree as particularly evidenced by the fastigiate growth habit. These genetic traits can be consistently reproduced by asexual propagation.

SUMMARY OF THE INVENTION

The cultivar 'QAMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QAMTF' grown in Washington, Ga. These characteristics in combination distinguish 'QAMTF' as a new and distinct *Quercus alba* cultivar:

1. Upright branching.
2. Fastigiate structure.
3. Central leader.
4. Deeply lobed leaf with a somewhat blue hue.
5. Suitability for commercial digging and transplanting.

PARENT COMPARISON

The parents cannot be identified.

COMMERCIAL COMPARISON

The cultivar 'QAMTF' can be compared to *Quercus alba* 'Repanda Michx', not patented. The varieties are similar in most horticultural characteristics. The new variety, however differs in the following:

1. The new variety has a much narrower canopy, with a central leader not consistently found in this comparator.
2. Foliage of the new variety is more deeply lobed and darker than foliage of this comparator.

BRIEF DESCRIPTION OF THE PHOTOGRAPHS

The accompanying photograph in FIG. 1 illustrates a typical tree of the new variety at about 3 years of age.

Figure 1:
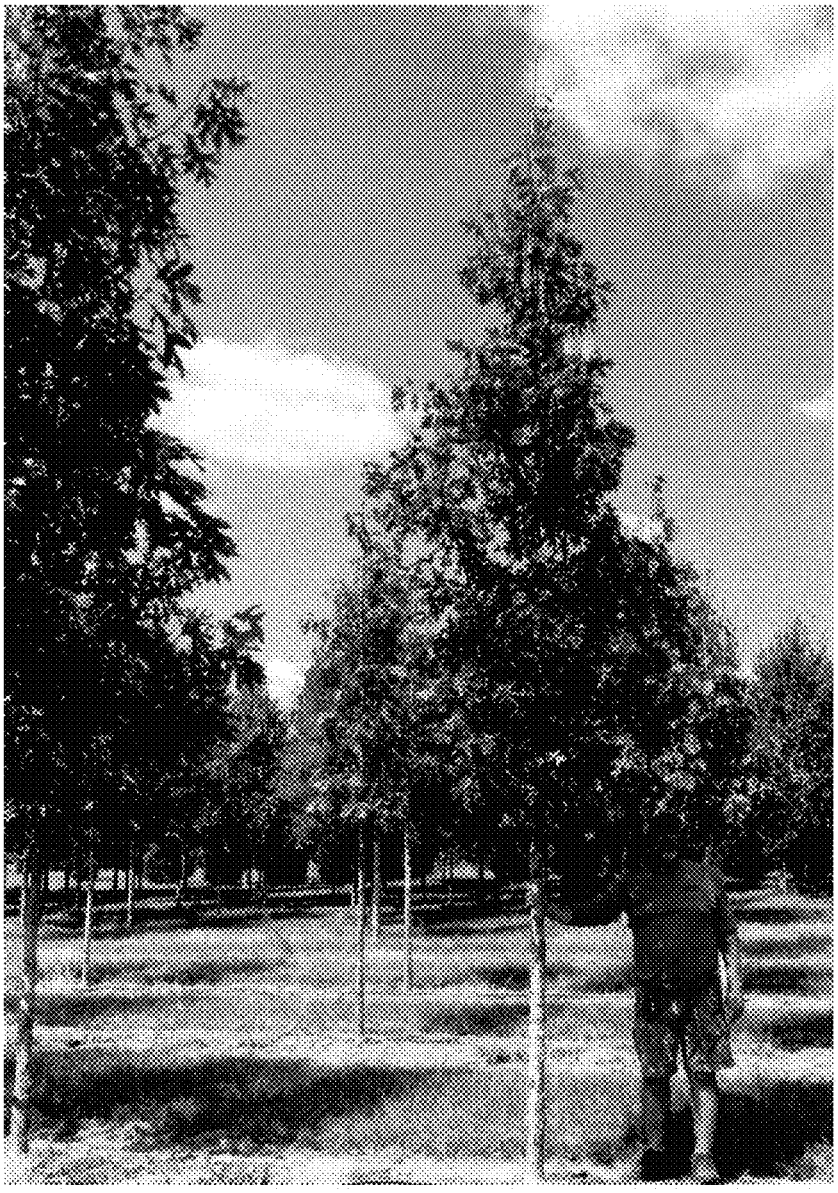
Figure 2:
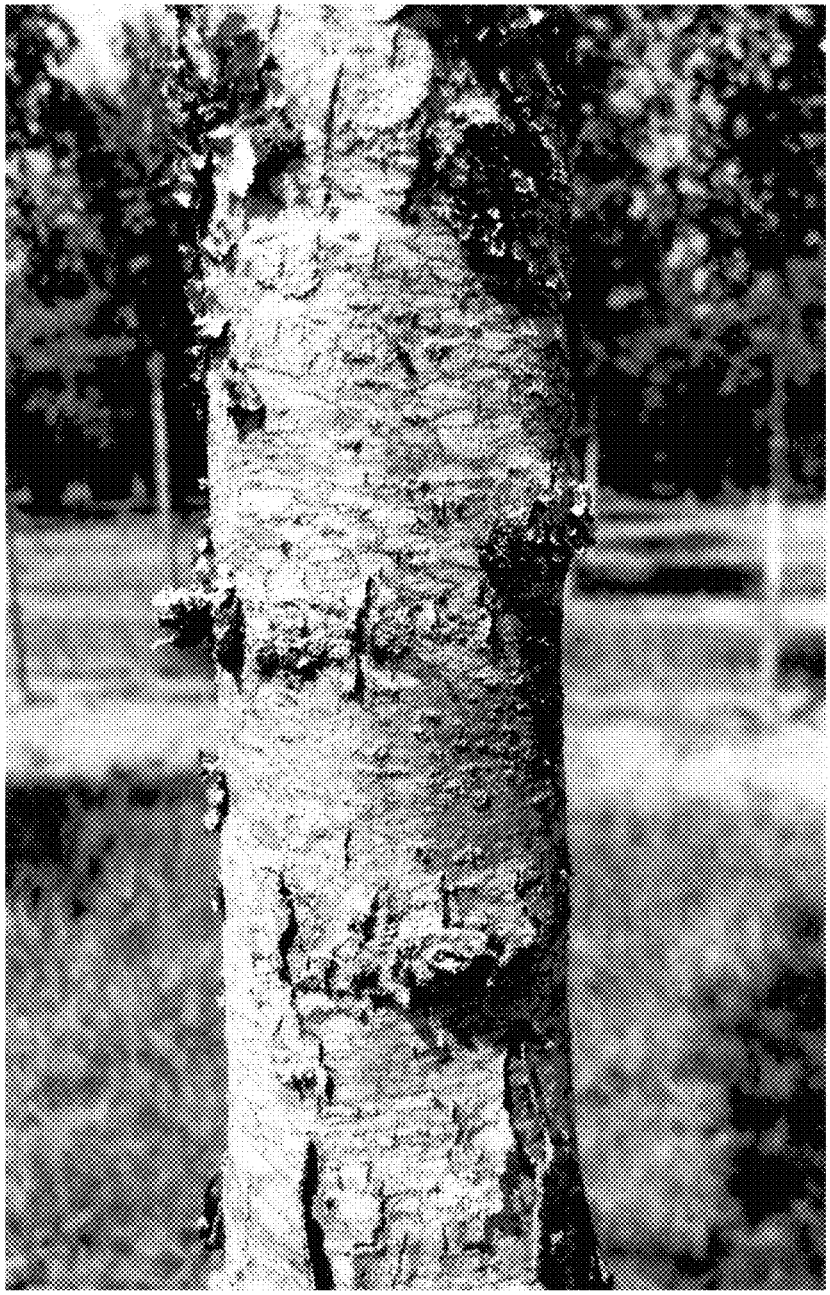
FIG. 2 illustrates a close-up view of the trunk.
Figure 3:
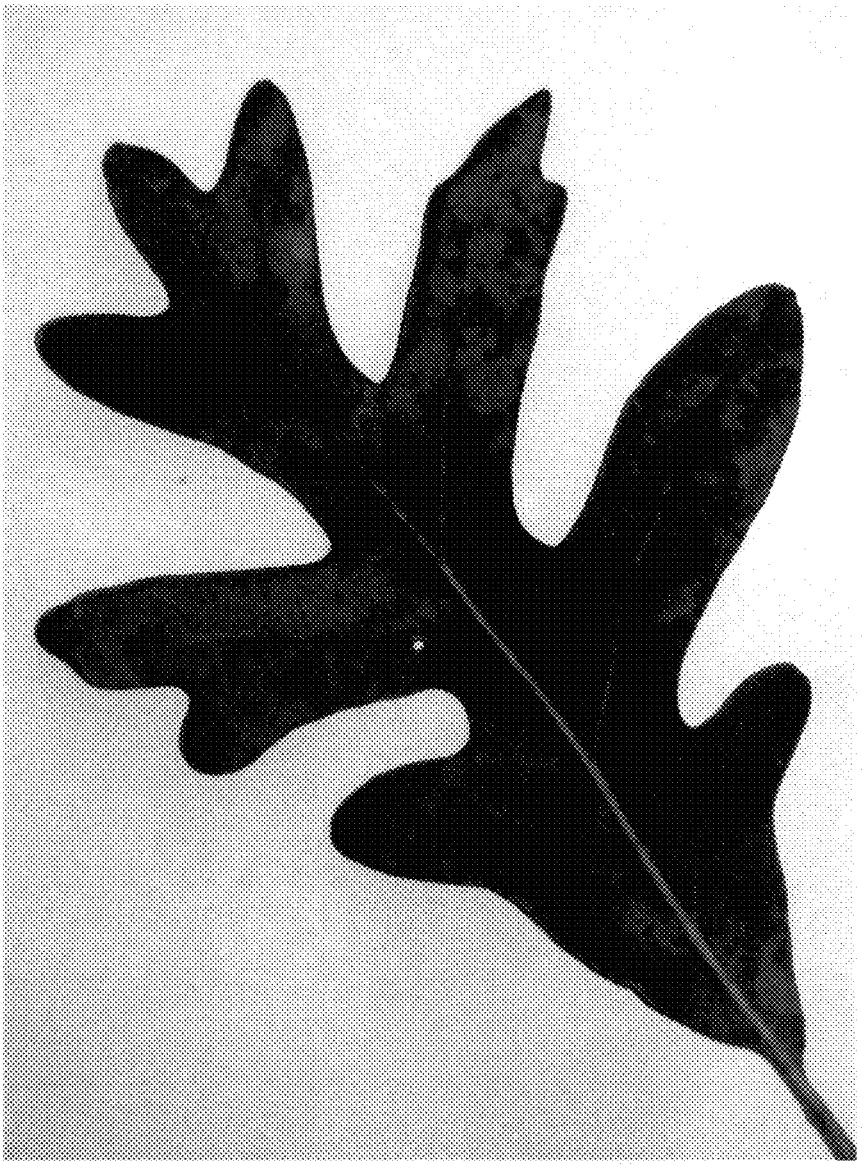
FIG. 3 illustrates typical foliage of the new variety.
Figure 4:
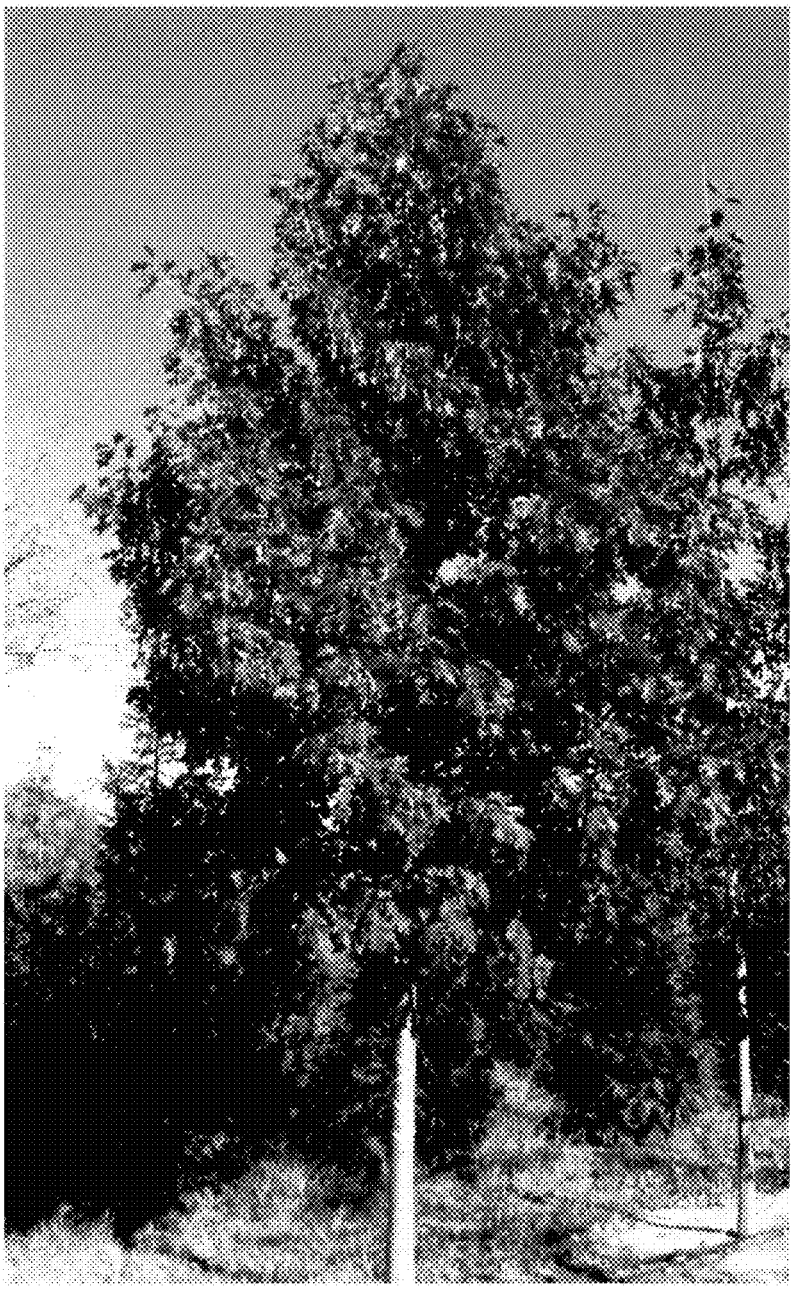
FIG. 4 illustrates Fall foliage color of 'QAMTF'. The tree in FIG. 4 is approximately 4 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QAMTF' plants grown outdoors and in a nursery in Washington, Ga. Plants are approximately 2 years old, fieldgrown. Temperatures ranged from 2° C. to 10° C. at night to 18° C. to 37° C. during the day. Measurements and numerical values represent averages of typical plant types. Botanical classification: *Quercus alba* 'QAMTF'.

PROPAGATION

Cleft grafting.

Root description: Woody. Brown roots not accurately measured with an R.H.S. Colour chart.

TREE

Growth habit: Deciduous fastigiate tree.

Height: Approximately 18 feet at 4 to 5 years. Approximately 22 feet at 10 years.

Spread: Approximately 5 feet at 4 years.

Growth rate: Rapid.

Branch characteristics:

*Length*.—Average Range 50 to 75 cm.

*Diameter*.—Average 2 cm.

*Color*.—Near RHS Greyed-Green 194A flushed Greyed-Purple 183C.

*Texture*.—Smooth.

*Angle*.—Acute, 45° or less.

*Aspect*.—Straight.

Trunk characteristics:

*Diameter*.—About 3 inches measured at approximately 3 inches above soil level at 4 years.

*Color*.—Bark near RHS Greyed-Green 196D with blotches near Greyed-Green 195C. Under bark colored near Greyed-Orange 165D.

*Surface texture*.—Rough bark, weakly to moderately peeling

FOLIAGE

Leaf:

*Arrangement*.—Alternate.

*Shape*.—Overall ovate, deeply lobed, 7 to 9 lobes.

*Average length*.—Approximately 12 to 14 cm excluding petiole.

*Average width*.—Approximately 6 to 8 cm.

*Apex*.—Acute.

*Base*.—Obtuse or asymmetrical cordate.

*Margin*.—Deeply lobed with sharp tips at the apex of each lobe. Sinuses about 1.5 to 2.2 cm deep.

*Texture of top surface*.—Glabrous.

*Texture of lower surface*.—Glabrous.

*Color*.—Young foliage: Upper side: Near RHS Green 137B. Under side: Near RHS Green 137B. Mature foliage: Upper side: Near RHS Green 139A with overlay Green 131A. Under side: Near RHS Green 139A. Fall foliage: Upper side: Near RHS Greyed-Orange 175C completely overlayed with Greyed-Red 181A, faint tinges of Greyed-Purple 185A present on oldest Fall leaves. Under side: Near RHS Greyed-Orange 175C overlayed with Greyed-Red 181A.

*Venation*.—Type: Pinnate. Color: Venation color upper side: Near RHS Yellow-Green N144B. Venation color under side: Near RHS Yellow-Green N144B.

*Petiole*.—Length: Average 22 mm. Diameter: Average 2 mm. Color: Upper side: Near RHS Yellow-Green N144A. Under side: Near RHS Yellow-Green N144A.

Stipule:

*Arrangement*.—Opposite, occurring in pairs.

*Shape*.—Oblong to kidney-shaped.

*Average length*.—Approximately 1.8 cm.

*Average width*.—Approximately 1 cm.

*Apex*.—Rounded

*Base*.—Truncate.

*Margin*.—Entire.

*Texture of top surface*.—Glabrous.

*Texture of lower surface*.—Glabrous.

*Color*.—Transparent Yellow-Green N144B with veins near Green 137B.

FLOWER

Flowering begins: Around early Spring in Georgia, generally around the time of foliage emergence. Individual male and female catkins.

Male catkins: About 5 cm to 10 cm long, about 7 to 12 mm wide. Weeping. Colored near RHS Yellow-Green 151A, turning Yellow-Green 154C flushed Greyed-Red 183A.

Female catkins: Semi-erect, About 2 cm long and approximately 4 mm wide. Colored near Yellow-Green 154D turning Greyed-Red 183A.

OTHER CHARACTERISTICS

Acorn:

*Length*.—Average about 1.6 cm.

*Diameter*.—Average about 1 cm.

*Cup coverage*.—About 20%.

*Immature color*.—Nut near Yellow-Green 144C flushed N144A. Cup Yellow-Green 146D flushed Grey-Brown 199B.

*Petiole*.—About 1 cm long, 2 mm in diameter. Colored near Grey-Brown N199A. Glabrous.

Disease/pest resistance: Neither resistance nor susceptibility to normal diseases and pests of *Quercus* has been observed.

Drought tolerance: No tolerance for drought observed. *Quercus alba* can be moderately drought tolerance once established.

Temperature tolerance: USDA Zones 3 through 9.

What is claimed is:

1. A new and distinct cultivar *of Quercus alba* tree named 'QAMTF' as herein illustrated and described.

* * * * *